(12) United States Patent
Levin et al.

(10) Patent No.: US 6,169,215 B1
(45) Date of Patent: Jan. 2, 2001

(54) PRODUCTION OF PHENOL

(75) Inventors: Doron Levin, Bala Cynwyd; Jose G. Santiesteban; James C. Vartuli, both of West Chester, all of PA (US)

(73) Assignee: Mobil Oil Corporation, Fairfax, VA (US)

( * ) Notice: Under 35 U.S.C. 154(b), the term of this patent shall be extended for 0 days.

(21) Appl. No.: 09/275,749

(22) Filed: Mar. 25, 1999

(51) Int. Cl.$^7$ ...................................... C07C 37/08
(52) U.S. Cl. .................. 568/798; 568/385; 568/485; 568/741; 568/754; 568/768
(58) Field of Search .................... 568/798, 385, 568/768, 741, 754, 485

(56) References Cited

U.S. PATENT DOCUMENTS

| | | | |
|---|---|---|---|
| 4,490,565 | * 12/1984 | Chang et al. | 568/798 |
| 4,490,566 | * 12/1984 | Chang et al. | 568/798 |
| 4,870,217 | * 9/1989 | Knifton | 568/798 |
| 4,898,995 | * 2/1990 | Knifton et al. | 568/798 |
| 5,113,034 | * 5/1992 | Soled et al. | 585/510 |

FOREIGN PATENT DOCUMENTS 0 492 807 * 7/1992 (EP).

* cited by examiner

Primary Examiner—Sreeni Padmanabhan

(57) ABSTRACT

A process for producing phenol and acetone from cumene hydroperoxide is described in which the cumene hydroperoxide is contacted with a solid-acid catalyst produced by calcining a source of a Group IVB metal oxide with a source of an oxyanion of a Group VIB metal at a temperature of at least 400°C.

9 Claims, No Drawings

PRODUCTION OF PHENOL

BACKGROUND OF THE INVENTION

1. Field of the Invention

This invention relates to the production of phenol and more particularly to a process for producing phenol and acetone from cumene hydroperoxide.

2. Description of the Prior Art

Phenol is an important organic chemical with a wide variety of industrial uses. It is used, for example, in the production of phenolic resins, bisphenol-A and caprolactam. A number of processes are currently in use for the production of phenol but the single process providing the largest proportion of the total production capacity is the cumene process which now accounts for over three quarters of the total U.S. production. The basic reaction involved in this process is the cleavage of cumene hydroperoxide into phenol and acetone:

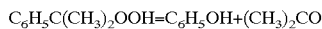

The reaction takes place under acid conditions with the yield of both phenol and acetone generally being 40 percent or more.

On an industrial scale, the cumene hydroperoxide is usually treated with dilute sulphuric acid (5 to 25 percent concentration) at a temperature of about 50 to 70° C. After the cleavage is complete, the reaction mixture is separated and the oil layer distilled to obtain the phenol and acetone together with cumene, alpha-methylstyrene, acetophenone and tars. The cumene may be recycled for conversion to the hydroperoxide and subsequent cleavage. The phenol produced in this way is suitable for use in resins although further purification is required for a pharmaceutical grade product.

Although the process described above is capable of producing both phenol and acetone in good yields, it would be desirable to find a process which would reduce the need for the product separation and purification steps which are inherent in a homogeneous process and would avoid the need for environmentally hazardous liquid acids.

The heterogeneous cleavage of cumene hydroperoxide (CHP) over various solid acid catalysts has already been reported. For example, U.S. Pat. No. 4,490,565 discloses the use of zeolite beta in the cleavage of cumene hydroperoxide, whereas U.S. Pat. No. 4,490,566 discloses the use of a Constraint Index 1-12 zeolite, such as ZSM-5, and EP-A-492807 discloses the use of faujasite in the same process. The use of smectite clays in the acid-catalyzed decomposition of cumene hydroperoxide is described in U.S. Pat. No. 4,870,217.

U.S. Pat. No. 4,898,995 discloses a process for the coproduction of phenol and acetone by reacting cumene hydroperoxide over a heterogeneous catalyst consisting of either an ion exchange resin having sulfonic acid functionality or a heteropoly acid, such as 12-tungstophosphoric acid, on an inert support, such as silica, alumina, titania and zirconia. Such heteropoly acid catalysts are generally used as their hydrates, and as such are inherently unstable at temperatures in excess of 350° C.

None of the solid-acid catalysts currently proposed for cumene hydroperoxide cleavage exhibit the required combination of activity and selectivity to provide an acceptable replacement for sulfuric acid.

SUMMARY OF THE INVENTION

The present invention is directed to a process for producing phenol and acetone from cumene hydroperoxide, wherein the process comprises the step of contacting cumene hydroperoxide with a solid-acid catalyst produced by calcining a source of a Group IVB metal oxide with a source of an oxyanion of a Group VIB metal at a temperature of at least 400° C.

The process of the invention can achieve at or near 100% conversion of cumene hydroperoxide at long on-stream times with high selectivity to phenol and acetone and with extremely low coproduction of impurities such as 4-cumylphenol, 2,4-diphenyl-4-methyl-1-pentene, and mesityl oxide.

Preferably, said temperature is at least 600° C. and more preferably is 700–850° C.

Preferably, Group IVB metal oxide is selected from zirconia and titania.

Preferably, said Group VIB metal oxyanion is selected from oxyanions of chromium, molybdenum and tungsten.

Preferably, said solid acid catalyst also contains a further metal selected from Group IB, VIIB and VII metals, and preferably selected from iron, manganese and copper.

Preferably, said contacting step is conducted at a temperature of 20 to 150° C. and a pressure of atmospheric to 1000 psig and more preferably at a temperature of 40 to 120° C. and a pressure of atmospheric to 400 psig.

DESCRIPTION OF SPECIFIC EMBODIMENTS

The process of the invention uses a solid acid catalyst comprising an oxide of a Group IVB metal modified with an oxyanion or oxide of a Group VIB metal by calcination of the oxide species at a temperature of at least 400° C. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; and in an article by K. Arata and M. Hino in *Proceedings 9th International Congress on Catalysis*, Volume 4, pages 1727–1735 (1988).

For the purposes of the present disclosure, the expression, Group IVB metal oxide modified with an oxyanion of a Group VIB metal, is intended to connote a material comprising, by elemental analysis, a Group IVB metal, a Group VIB metal and oxygen, but with more acidity than a simple mixture of separately formed Group IVB metal oxide mixed with a separately formed Group VIB metal oxide or oxyanion. Such enhanced acidity is believed to result from an actual chemical interaction between the Group IVB metal oxide and the Group VIB metal oxyanion.

In the aforementioned article by K. Arata and M. Hino, when discussing the generation of acidity of sulfated Group IVB metal oxides, it is suggested that solid superacids are formed when sulfates are reacted with hydroxides or oxides of certain metals, e.g., Zr. These superacids are said to have the structure of a bidentate sulfate ion coordinated to the metal, e.g., Zr. In this article, it is further suggested that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure. It is further suggested that tungsten oxide combines with zirconium oxide compounds to create superacid sites at the time a tetragonal phase is formed.

Although it is believed that the present catalysts may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

The present catalysts may have calculated mole ratios, expressed in the form of $XO_2/YO_3$, where X is at least one Group IVB metal (i.e., Ti, Zr, and Hf) and Y is at least one Group VIB metal (i.e., Cr, Mo, or W), of up to 1000, e.g., up to 300, e.g., from 2 to 100, e.g., from 4 to 30, although it is to be appreciated that these forms of oxides, i.e., $XO_2$ and $YO_3$, may not actually be present in the catalyst of the invention. It is to be appreciated that mixtures of Group IVB metals and/or mixtures of Group VIB metals may be present in the catalyst of the invention.

The Group IVB metal oxide is preferably selected from titania, zirconia and hafnia, with zirconia being most preferred, while the Group VIB metal oxyanion is preferably selected from oxyanions of chromium, moybdenum and tungsten, with oxyanions of tungsten being most preferred. The Group IVB and Group VIB metal species present in the final catalyst are not limited to any particular valence state and may be present in any positive oxidation value possible for the respective species. For example, when the catalyst contains tungsten, subjecting the catalyst to reducing conditions may be used to lower reduce the valence state of the tungsten and modify the overall activity of the catalyst.

Suitable sources of the Group IVB metal oxide include compounds capable of generating such oxides during calcination with the Group VIB metal oxyanion, such as oxychlorides, chlorides, and nitrates. A further suitable source of the Group IVB metal oxide include salts containing the cation of the Group IVB metal, such as halides, nitrates, and acetates. Alkoxides may also be used as the sources of the Group IVB metal oxide, for example zirconium n-propoxide and titanium i-propoxide. A preferred source of the Group IVB metal oxide is hydrated zirconia. The expression, hydrated zirconia, is intended to connote a material comprising zirconium atoms covalently linked to other zirconium atoms via bridging oxygen atoms and further comprising available surface hydroxyl groups. These available surface hydroxyl groups are believed to react with the oxyanion of the Group VIB metal to form the present acidic catalyst component. Hydrated zirconia can be formed by precalcination of $Zr(OH)_4$ at a temperature of about 100° C. to about 400° C.

It has been found that hydrothermal treatment of the hydrated Group IVB metal oxide, such as hydrated zirconia, promotes the interaction with the Group VIB metal oxyanion, such as tungstate. The hydrothermal treatment conditions may include a temperature of at least 80° C., e.g., at least 100° C. The hydrothermal treatment may take place in a sealed vessel at greater than atmospheric pressure. However, a preferred mode of treatment involves the use of an open vessel under reflux conditions. Agitation of hydrated Group IVB metal oxide in the liquid medium, e.g., by the action of refluxing liquid and/or stirring, promotes the effective interaction of the hydrated oxide with the liquid medium. The duration of the contact of the hydrated oxide with the liquid medium may be at least 1 hour, e.g., at least 8 hours. The liquid medium for this treatment may have a pH of about 7 or greater, e.g., 9 or greater. Suitable liquid media include water, hydroxide solutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$), pyridine and its derivatives, and alkyl/hydroxyl amines.

Suitable sources for the oxyanion of the Group VIB metal include, but are not limited to, ammonium metatungstate or metamolybdate, tungsten or molybdenum chloride, tungsten or molybdenum carbonyl, tungstic or molybdic acid and sodium tungstate or molybdate.

Other metals, such as metals of Groups IB, VIIB and VII, and preferably iron, manganese and/or copper, may optionally be added to the present catalyst to alter its catalytic properties.

The present catalyst may be prepared, for example, by impregnating the hydrothermally treated hydrated oxide of the Group IVB metal with an aqueous solution containing an anion of the Group VIB metal, preferably tungstate or molybdate, followed by drying. The resulting material is then calcined as described below.

Alternatively, the present catalyst may be prepared by combining a first liquid solution comprising a source of Group IVB metal oxide with a second liquid solution comprising a source of an oxyanion of a Group VIB. This combination of two solutions takes place under conditions sufficient to cause co-precipitation of the modified oxide material as a solid from the liquid medium. Alternatively, the source of the Group IVB metal oxide and the source of the oxyanion of the Group VIB metal may be combined in a single solution. This solution may then be subjected to conditions sufficient to cause co-precipitation of the solid modified oxide material, such as by the addition of a precipitating reagent to the solution. Water is a preferred solvent for these solutions. The temperature at which the liquid medium is maintained during the co-precipitation may be less than about 200° C., e.g., from about 0° C. to about 200° C. and preferably from about 50° C. to about 100° C. The resulting material is dried and then calcined as described below.

Calcination of the coprecipitated or impregnated oxides is effected, preferably in an oxidizing atmosphere, at a temperature of at least 400° C., preferably at least 600° C., and more preferably from about 700° C. to about 850° C., and most preferably from about 750° C. to about 825° C. The calcination time may be up to 48 hours, preferably for about 0.5–24 hours, and more preferably for about 1.0–10 hours. In a most preferred embodiment, calcination is carried out at about 800° C. for about 1 to about 3 hours. The optional Group IB, VIIB and/or VIII component of the catalyst may be added after or before calcination by techniques known in the art, such as impregnation, coimpregnation, coprecipitation and physical admixture.

The catalyst may be subjected to a final calcination under conventional conditions in order to dehydrate the catalyst and to confer the required mechanical strength on the catalyst. Prior to use, the catalyst may be subjected to presulfiding, e.g., by heating in the presence of hydrogen sulfide, to convert oxide forms of the metal components to their corresponding sulfides.

The present catalyst can be shaped into a wide variety of particle sizes. Generally speaking, the particles can be in the form of a powder, a granule, or a molded product, such as an extrudate. In cases where the catalyst is molded, such as by extrusion, the catalyst can be extruded before drying, or partially dried and then extruded. The present catalyst may be extruded by itself, or it may be composited with a matrix material to form the finished form of the catalyst and for this purpose conventional matrix materials such as alumina, silica-alumina and silica are suitable with preference given to silica as a non-acidic binder. Other binder materials may be used, for example, titania, zirconia and other metal oxides or clays. The active catalyst may be composited with the matrix in amounts from 80:20 to 20:80 by weight, e.g., from 80:20 to 50:50 active catalyst:matrix. Compositing may be done by conventional means including mulling the materials together followed by extrusion or pelletizing into the desired finished catalyst particles.

The cleavage reaction of the invention is effected by contacting the cumene hydroperoxide with the solid oxide catalyst described above in the liquid phase at a temperature of 20 to 150° C., preferably 40 to 120° C., and a pressure of atmospheric to 1000 psig, preferably atmospheric to 400 psig. To effect the contacting of the cumene hydroperoxide, the solid oxide catalyst described above may be contained in a stationary or fluidized bed, and the contacting operation may take place continuously or batch-wise. If the contacting takes place continuously, the LHSV based on cumene hydroperoxide is within the range of 0.1 to 100 $hr^{-1}$, preferably 1 to 50 $hr^{-1}$. If the contacting takes place batch-wise, the residence time is within the range of 1 to 180 min, preferably 1 to 25 min. The cumene hydroperoxide is preferably dissolved in an organic solvent inert to the cleavage reaction, such as benzene, toluene, cumene and most preferably acetone. The use of a solvent is preferred so as to assist in dissipating the heat of reaction (about 60 kcal/mol).

The invention will now be more particularly described with reference to the following Examples.

EXAMPLE 1

Five hundred grams of $ZrOCl_2.8H_2O$ were dissolved with stirring in 3.0 liters of distilled water. To this solution was added 7.6 g of $FeSO_4.7H_2O$. Another solution containing 260 g of concentrated $NH_4OH$, 54 g of $(NH_4)_6 H_2W_{12}O_{40}.xH_2O$ and 2940 ml of distilled water prepared. Both solutions were heated to 60 ° C. and the heated solutions were combined at a rate of 50 ml/min using nozzle mixing. The pH of the final composite was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A sample of the dried product was calcined to 800° C. in flowing air for 3 hours.

EXAMPLE 2

To a 250-ml round bottom flask fitted with a condenser, stirrer and dropping funnel, and located in a water bath for temperature control, was charged a mixture of 100.0 g of acetone and 1.00 g of the catalyst of Example 1. The mixture was heated to reflux (57° C.) with stirring, and 50.0 g of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 g/min. Following addition of the CHP solution, small samples (~0.2 ml) of the reactant solution were withdrawn at regular intervals, filtered, and analyzed by GC.

Table I below shows the composition (mass %) of the reactant solution at 2 and 20 minutes after the addition of the CHP was complete.

TABLE I

|  | Feed | 2 min | 20 min |
|---|---|---|---|
| Acetone | 66.67 | 78.06 | 77.92 |
| Mesityl Oxide | 0.0 | 0.00 | 0.00 |
| Cumene | 2.56 | 2.62 | 2.64 |
| Phenol | 0.09 | 16.51 | 16.70 |

TABLE I-continued

|  | Feed | 2 min | 20 min |
|---|---|---|---|
| α-Methyl Styrene | 0.07 | 1.00 | 1.35 |
| Acetophenone | 0.69 | 0.67 | 0.65 |
| 2-Phenyl-2-Propanol | 2.29 | 0.79 | 0.39 |
| Cumene Hydroperoxide | 26.93 | 0.03 | 0.01 |
| CHP Conversion |  | 99.87% | 99.95% |

EXAMPLE 3

Five hundred grams of $ZrOCl_2.8H_2O$ were dissolved with stirring in 3.0 liters of distilled water. To this solution was added 7.6 g of $FeSO_4.7H_2O$. Another solution containing 260 g of concentrated $NH_4OH$, 66 g of $(NH_4)_6 Mo_7O_{24}.4H_2O$ and 3.0 liters of distilled water was prepared. Both solutions were heated to 60° C. and the heated solutions were combined at the rate of 50 ml/min using a nozzle mixing. The pH of the final composite was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A sample of the dried product was calcined to 800° C. in flowing air for 3 hours to produce an acidic oxide catalyst containing a nominal 1 wt. % Fe/16 wt. % Mo on zirconia.

EXAMPLE 4

To a 250-ml round bottom flask fitted with a condenser, stirrer and dropping funnel, and located in a water bath for temperature control, was charged a mixture of 100.0 g of acetone and 1.00 g of the catalyst of Example 3. The mixture was heated to reflux (57° C.) with stirring, and 50.0 g of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 g/min. Following addition of the CHP solution, small samples (~0.2 ml) of the reactant solution were withdrawn at regular intervals, filtered, and analyzed by GC.

Table II below shows the composition (mass %) of the reactant solution at 4 minutes after the addition of the CHP was complete.

TABLE II

|  | Feed | 2 min | 20 min |
|---|---|---|---|
| Acetone | 66.67 | 77.68 | 77.71 |
| Mesityl Oxide | 0.0 | 0.00 | 0.00 |
| Cumene | 2.56 | 2.64 | 2.65 |
| Phenol | 0.09 | 16.83 | 16.87 |
| α-Methyl Styrene | 0.07 | 0.97 | 1.34 |
| Acetophenone | 0.69 | 0.73 | 0.68 |
| 2-Phenyl-2-Propanol | 2.29 | 0.84 | 0.35 |
| Cumene Hydroperoxide | 26.93 | 0.03 | 0.01 |
| CHP Conversion |  | 99.88% | 99.95% |

EXAMPLE 5

Three hundred and sixty grams of $ZrO(NO_3)_2.8H_2O$ were dissolved with stirring in 3.0 liters of distilled water. Another solution containing 260 9 of conc. $NH_4OH$ and 3.0 liters of distill water was prepared. Both solutions were heated to 60° C. These two heated solutions were combined at the rate of 50 ml/min using a nozzle mixing. The pH of the final composite was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A solution of 5.3 g of $(NH_4)_6W_{12}O_{39} \cdot xH_2O$ in 15.0 g of DI water was prepared added dropwise on to 29.5 g of the freshly prepared zirconia. This material was dried overnight at 85° C. A portion of this catalyst was calcined at 800° C. in flowing air for 3 hours.

EXAMPLE 6

To a 250-ml round bottom flask fitted with a condenser, stirrer and dropping funnel, and located in a water bath for temperature control, was charged a mixture of 100.0 g of acetone and 1.00 g of the catalyst of Example 5. The mixture was heated to reflux (57° C.) with stirring, and 50.0 9 of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 g/min. Following addition of the CHP solution, small samples (~0.2 ml) of the reactant solution were withdrawn at regular intervals, filtered, and analyzed by GC.

Table III below shows the composition (mass %) of the reactant solution at 2 and 20 minutes after the addition of the CHP was complete.

TABLE III

|  | Feed | 2 min | 20 min |
| --- | --- | --- | --- |
| Acetone | 66.67 | 77.73 | 77.70 |
| Mesityl Oxide | 0.0 | 0.00 | 0.00 |
| Cumene | 2.56 | 2.65 | 2.64 |
| Phenol | 0.09 | 16.63 | 16.82 |
| α-Methyl Styrene | 0.07 | 0.71 | 1.06 |
| Acetophenone | 0.69 | 0.78 | 0.74 |
| 2-Phenyl-2-Propanol | 2.29 | 1.12 | 0.68 |
| Cumene Hydroperoxide | 26.93 | 0.08 | 0.03 |
| CHP Conversion |  | 99.70% | 99.91% |

EXAMPLE 7

Thirty-eight grams of $TiOSO_4 \cdot xH_2SO_4$ were dissolved with stirring in 300 g of distilled water. Another solution containing 36.4 g of conc. $NH_4OH$, 5.4 g of $(NH_4)_6W_{12}O_{39} \cdot xH_2O$ and 300 g of distill water was prepared, and was slowly added at room temperature to the first solution. The pH of the final composite was adjusted to approximately 9 by the addition of concentrated ammonium hydroxide. This slurry was then put in a polypropylene bottle and placed in a steambox (100° C.) for 72 hours. The product formed was recovered by filtration, washed with excess water, and dried overnight at 85° C. A portion of this solid material was calcined to 600° C. in flowing air for 3 hours to produce an acidic oxide catalyst containing a nominal 16 wt. % W on titania.

EXAMPLE 8

To a 250-ml round bottom flask fitted with a condenser, stirrer and dropping funnel, and located in a water bath for temperature control, was charged a mixture of 100.0 g of acetone and 1.00 g of the catalyst of Example 7. The mixture was heated to reflux (57° C.) with stirring, and 50.0 g of "80%" cumene hydroperoxide (CHP) solution (analyzed as 80.8% CHP, 7.7% cumene, 6.9% 2-phenyl-2-propanol, 2.1% acetophenone) was added dropwise at an approximate rate of 2 g/min. Following addition of the CHP solution, small samples (~0.2 ml) of the reactant solution were withdrawn at regular intervals, filtered, and analyzed by GC.

Table IV below shows the composition (mass %) of the reactant solution at 2 and 20 minutes after the addition of the CHP was complete.

TABLE IV

|  | Feed | 2 min | 20 min |
| --- | --- | --- | --- |
| Acetone | 66.67 | 77.71 | 77.79 |
| Mesityl Oxide | 0.0 | 0.00 | 0.00 |
| Cumene | 2.56 | 2.62 | 2.63 |
| Phenol | 0.09 | 16.57 | 16.69 |
| α-Methyl Styrene | 0.07 | 0.96 | 1.36 |
| Acetophenone | 0.69 | 0.70 | 0.66 |
| 2-Phenyl-2-Propanol | 2.29 | 0.84 | 0.36 |
| Cumene Hydroperoxide | 26.93 | 0.03 | 0.02 |
| CHP Conversion |  | 99.88% | 99.94% |

EXAMPLE 9

To a continuous plug-flow reactor was charged 0.5 cm³ of the catalyst of Example 1, diluted with 2 cm³ of inert sand. The catalyst bed was pretreated with a stream of acetone at 80° C., and then a "80%" cumene hydroperoxide (CHP) solution, diluted with acetone was passed through the catalyst bed in the downflow mode at a series of feed flowrates. The reactor temperature was held constant at 80° C. and the pressure in the reactor was 50 psig. Product samples were collected at regular intervals and analyzed by GC.

The composition (mass %) of the feed and product solutions are summarized in Table V.

TABLE V

| Sample | LHSV hr⁻¹ (CHP basis) | Acetone | Cumene | Phenol | α-Methyl Styrene | Aceto-phenone | 2-Phenyl-2-Propanol | CHP |
| --- | --- | --- | --- | --- | --- | --- | --- | --- |
| Feed |  | 96.26 | 0.24 | 0.05 | 0.09 | 0.08 | 0.45 | 2.73 |
| 1 | 0.91 | 97.34 | 0.26 | 1.80 | 0.32 | 0.07 | 0.00 | 0.00 |
| 2 | 1.74 | 97.38 | 0.26 | 1.87 | 0.30 | 0.08 | 0.01 | 0.00 |
| 3 | 2.73 | 97.43 | 0.27 | 1.83 | 0.31 | 0.07 | 0.01 | 0.00 |
| 4 | 3.64 | 97.41 | 0.27 | 1.85 | 0.31 | 0.08 | 0.01 | 0.00 |
| 5 | 4.55 | 97.62 | 0.26 | 1.69 | 0.29 | 0.07 | 0.01 | 0.00 |

For all samples 1–5, the conversion of CHP was 100%. No heavy products such as 4-cumylphenol or 2,4-diphenyl-4-methyl-1-pentene were present in the product solutions.

Analysis of samples 1–5 also show that the dehydration of 2-phenyl-2-propanol into α-methyl syrene takes place simultaneously to the CHP decomposition reaction with dehydration levels >97%.

What we claim is:

1. A process for producing phenol and acetone from cumene hydroperoxide, wherein said process comprises the step of contacting cumene hydroperoxide with a solid-acid catalyst produced by calcining a source of a Group IVB metal oxide with a source of an oxyanion of a Group VIB metal at a temperature of at least 400° C.

2. The process of claim 1, wherein said temperature is at least 600° C.

3. The process of claim 1, wherein said temperature is 700–850° C.

4. The process of claim 1, wherein said Group IVB metal oxide is selected from zirconia and titania.

5. The process of claim 1, wherein said Group VIB metal oxyanion is selected from oxyanions of chromium, molybdenum and tungsten.

6. The process of claim 1, wherein said solid acid catalyst also contains a metal selected from Groups IB, VIIB, or VIII of the Periodic Table.

7. The process of claim 6, wherein said metal is iron, manganese and/or copper.

8. The process of claim 1, wherein said contacting step is conducted at a temperature of 20 to 150° C. and a pressure of atmospheric to 1000 psig.

9. The process of claim 1, wherein said contacting step is conducted at a temperature of 40 to 120° C. and a pressure of atmospheric to 400 psig.

* * * * *